United States Patent [19]

Sobel

[11] E Re. 28,724

[45] Reissued Feb. 24, 1976

[54] ISOPARAFFIN ALKYLATION WITH A LIGHTER OLEFIN AND SUBSEQUENTLY WITH A HEAVIER OLEFIN

[75] Inventor: Jay E. Sobel, Highland Park, Ill.

[73] Assignee: Universal Oil Products Co., Des Plaines, Ill.

[22] Filed: Apr. 28, 1975

[21] Appl. No.: 572,600

Related U.S. Patent Documents

Reissue of:

[64] Patent No.: 3,780,131
Issued: Dec. 18, 1973
Appl. No.: 269,907
Filed: July 7, 1972

[52] U.S. Cl. ..... 260/683.45; 260/683.48
[51] Int. Cl.[2] ..... C07C 3/54
[58] Field of Search..... 260/683.45, 683.48, 683.49

[56] References Cited

UNITED STATES PATENTS

| | | | |
|---|---|---|---|
| 2,312,539 | 3/1943 | Frey | 260/683.45 |
| 2,415,717 | 2/1947 | Watkins et al. | 260/683.45 |
| 2,427,293 | 9/1947 | Matuszak | 260/683.61 |
| 2,476,750 | 7/1949 | Matuszak | 260/683.45 |
| 2,820,073 | 1/1958 | Dixon et al. | 260/683.45 |
| 3,211,803 | 10/1965 | Chapman | 260/683.49 |
| 3,236,912 | 2/1966 | Phillips | 260/683.49 |
| 3,787,518 | 1/1974 | Anderson | 260/683.45 |

*Primary Examiner*—Delbert E. Gantz
*Assistant Examiner*—G. J. Crasanakis
*Attorney, Agent, or Firm*—James R. Hoatson, Jr.; Thomas K. McBride; William H. Page, II

[57] ABSTRACT

A process for alkylating an isoparaffin with a lighter olefin and a heavier olefin by contacting the isoparaffin with the lighter olefin and a first alkylation catalyst in a first alkylation zone, contacting the hydrocarbon effluent from the first alkylation zone with the heavier olefin and a second alkylation catalyst in a second alkylation zone, and recovering the product of the process from the hydrocarbon effluent from the second alkylation zone.

9 Claims, 1 Drawing Figure

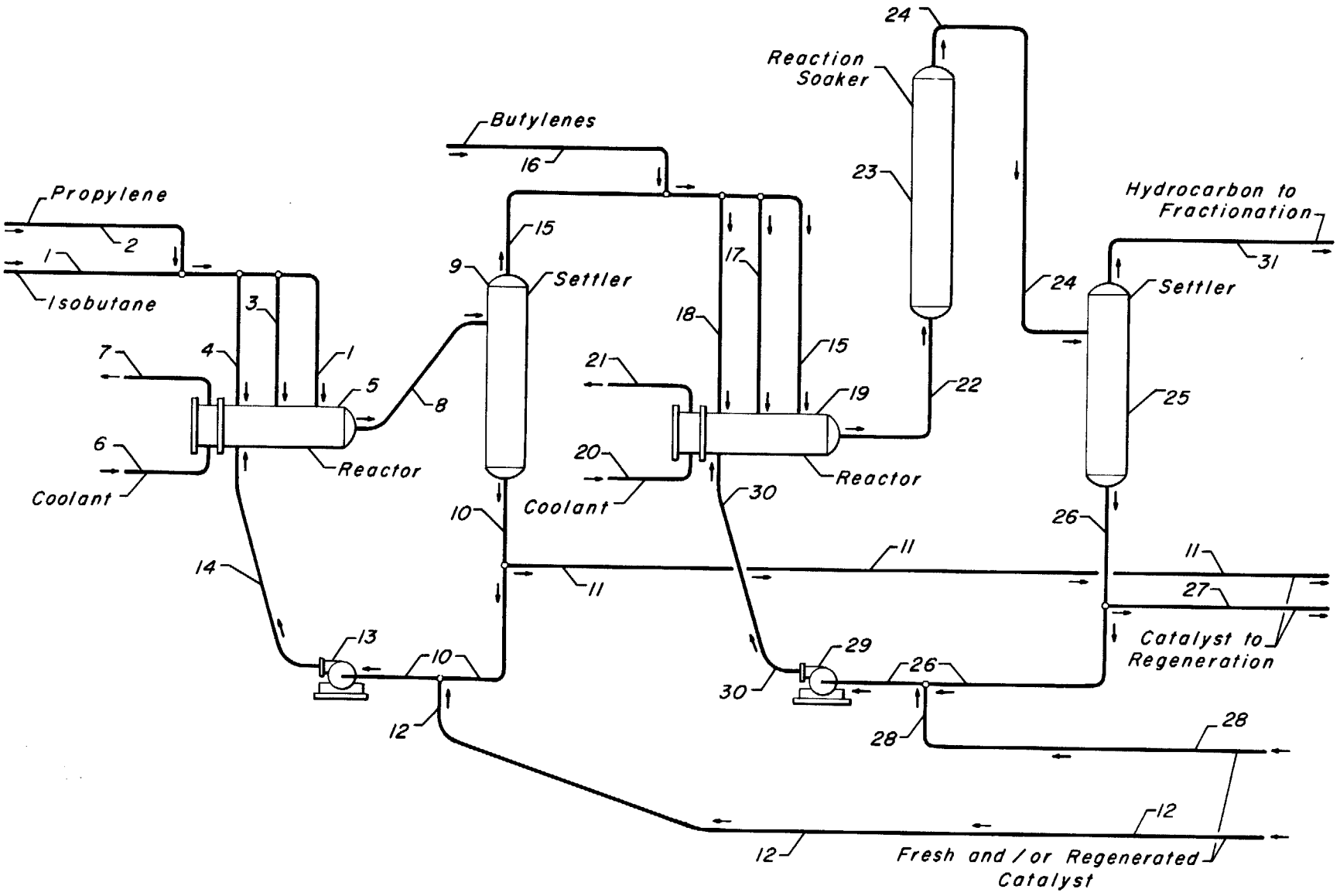
Hydrocarbon to Fractionation
Settler
Catalyst to Regeneration
Fresh and/or Regenerated Catalyst
Reaction Soaker
Reactor
Coolant
Settler
Butylenes
Reactor
Coolant
Propylene
Isobutane

ISOPARAFFIN ALKYLATION WITH A LIGHTER OLEFIN AND SUBSEQUENTLY WITH A HEAVIER OLEFIN

Matter enclosed in heavy brackets [ ] appears in the original patent but forms no part of this reissue specification; matter printed in italics indicates the additions made by reissue.

BACKGROUND OF THE INVENTION

This invention relates to a process for alkylating an alkylatable isoparaffinic hydrocarbon with olefinic hydrocarbons. More specifically, this invention relates to a process for producing an alkylation reaction product from an isoparaffinic reactant, a lighter olefinic reactant and a heavier olefinic reactant, utilizing acid-acting alkylation catalysts. This invention further relates to the process for producing an alkylation reaction product having superior qualities as a component of motor fuels, in comparison to the product produced by previously employed alkylation processes.

Alkylation of isoparaffinic hydrocarbons, such as isobutane, isopentane and the like, with olefinic hydrocarbons such as propylene, butylenes, amylenes, and the like, is well known as a commercially important method for producing gasoline boiling range hydrocarbons. The $C_5$—$C_{10}$ hydrocarbons generally produced by the alkylation reaction are termed "alkylate." Alkylate is particularly useful as a motor fuel blending stock because of its high motor octane and research octane ratings, such that it can be used to improve the overall octane ratings of gasolines to comply with the requirements of modern automobile motors. Such high octane products are particularly important in producing unleaded motor fuels of sufficient quality when it is desired not to employ alkyl lead compounds in the fuel to meet octane requirements. A continuing goal of the art is to provide an isoparaffin-olefin alkylation process which produces an alkylate product having higher motor and research octane ratings than is possible using conventional processes.

Recent trends in motor fuel requirements and projections of future requirements in this area indicate that the production of motor fuels distilling at end points below about 300° F. may be desirable and/or necessary to meet projected standards. Conventional isoparaffin-olefin alkylation processes do not have the capacity to produce an alkylate product having a distillation end point low enough to be useful in providing such low end point motor fuels. The process of the present invention provides a method whereby an alkylate product having a significantly lower distillation end point than possible using conventional processes may be produced, in addition to the increased value of the product of the present process resulting from octane rating improvements.

In general, commercial isoparaffin-olefin alkylation processes employ isobutane as the isoparaffin and propylene and/or butylenes as the olefins. Catalysts utilized include hydrogen fluoride, sulfuric acid and other like acidic or acid-acting materials. The isoparaffin, olefins and catalyst are typically contacted in an alkylation reactor, forming a reaction mixture. After the alkylation reaction is substantially complete, the reaction mixture is withdrawn from the reactor and is separated into hydrocarbon and catalyst phases in a separation zone, generally by settling in a settling vessel, and the catalyst thus separated is recycled to the reactor for further use. The hydrocarbon phase produced is further processed, for example, by fractionation, to recover the alkylate product and to separate unconsumed reactants, e.g., isoparaffin, for further use.

It has been found preferable to conduct isoparaffin-olefin alkylation processes at particular conditions of temperature and pressure, and at specific concentrations of reactants and catalysts in order to produce an optimum yield of high quality alkylate product. A large molar excess of isoparaffin, relative to olefin, in the reaction mixture, generally about 10:1 to about 30:1, is one of the conditions required to provide even an adequate product. It has been found desirable to employ as large an excess of isoparaffin as possible, since the quality of the alkylate product is improved thereby. Thus, a considerable amount of isoparaffin is generally recovered and recycled to the reactor after separation from the hydrocarbon phase of the reactor effluent. The large amount of isoparaffin which must accordingly be passed, unreacted, through the alkylation reactor and settler and separated from the alkylate product necessitates the use of fractionation equipment of large capacity in order to provide an adequate separation of the product alkylate from the isoparaffin to be recycled. Limitations on the amount of excess isoparaffin employed are primarily of an economic nature. The expense and difficulty of providing a large isoparaffin throughput and recycle may be obviated, in part, through the use of the process of this invention.

It is known that higher quality alkylate may be produced, in the alkylation of different molecular weight olefins such as propylene and butylenes, etc., with an isoparaffin, when one olefin, for example, propylene is separately alkylated with the isoparaffin at one set of reaction conditions while, for example, butylenes are alkylated with the isoparaffin at a different set of reaction conditions. However, it has been found necessary to maintain the same high molar excess of isoparaffin to olefin in both the propylene alkylation reaction and the butylenes alkylation reaction in order to provide an adequate product. The separate alkylation of, for example, $C_3$ and $C_4$ olefins has, therefore, been found uneconomical, because of the expense of providing separate reactors for the $C_3$ and $C_4$ olefins when combined with the above-noted expense and difficulties in handling the large molar excess of isoparaffin, to provide a high quality product.

SUMMARY OF THE INVENTION

It is an object of the present invention to provide a process for alkylating an isoparaffin with a lighter olefin and a heavier olefin. A further object of the present invention is to provide a process for producing a superior alkylation reaction product from a lighter olefin, a heavier olefin and an isoparaffin. Another object of the present invention is to provide an isoparaffin-olefin alkylation process having a reduced isoparaffin handling requirement, while maintaining a high isoparaffin concentration during the alkylation reaction.

In a broad embodiment, the present invention relates to a process for producing an alkylation reaction product from an isoparaffinic reactant, a lighter olefinic reactant and a heavier olefinic reactant which comprises the steps of: (a) contacting said isoparaffinic reactant and said lighter olefinic reactant with a first alkylation catalyst in a first alkylation zone at first alkylation conditions; (b) recovering from said first alkylation zone a first hydrocarbons stream which comprises a portion of said isoparaffinic reactant and a portion of said alkylation reaction product; (c) contacting said heavier olefinic reactant and at least a portion of said first hydrocarbons stream with a second alkylation catalyst in a second alklyation zone at second alkylation conditions; (d) recovering from said second alkylation zone a second hydrocarbons stream which comprises at least a portion of said alkylation reaction product; and (e) recovering said alkylation reaction product from said hydrocarbons stream.

I have discovered a method whereby a lighter olefinic reactant and a heavier olefinic reactant can be alkylated separately with an isoparaffin at different alkylation conditions preferred for separate alkylation of the two olefins, providing a superior reaction product from both olefins. Simultaneously, the amount of excess isoparaffin required for optimum alkylation conditions can be reduced. By passing the total charge of isoparaffinic reactant into a first alkylation reactor with the lighter olefinic reactant, charging the hydrocarbon effluent from the first reactor and the heavier olefinic reactant to a second alkylation reactor, and recovering the alkylate product from the hydrocarbon effluent from the second alkylation reactor, the separate alkylation of the ligher and heavier olefins can be accomplished with an optimum concentration of excess isoparaffin for both the reactions in both reactors without the necessity of providing separate isoparaffin supplies to the two reactors employed.

DESCRIPTION OF THE DRAWING

The attached drawing illustrates a particular embodiment of the present invention. In the embodiment shown, isobutane is employed as the isoparaffin, butylenes and propylene are employed as the heavier and lighter olefinic reactants, respectively, and hydrogen fluoride catalysts are employed in both alkylation reactors, the catalysts having different concentrations of hydrogen fluoride therein. The scope of the present invention is not limited to the embodiments illustrated thereby. Further objects, embodiments, and illustrations indicative of the broad scope of the present invention will be apparent to those skilled in the art from the description of the drawing and preferred embodiments of the invention hereinafter provided.

Referring to the drawing, isobutane is charged in conduit 1. The lighter olefinic reactant, comprising propylene, is charged through conduit 2 and passed in conduit 1 in admixture with isobutane. The mixture of propylene and isobutane is passed through conduit 1 and a portion thereof is diverted through conduits 3 and 4 and the reactants in conduits 1, 3 and 4 are passed separately into alkylation reactor 5 to insure thorough mixing in reactor 5. In alkylation reactor 5 the isoparaffin and olefin are contacted and thoroughly admixed, with high strength hydrogen fluoride catalyst comprising about 95% acid to form a reaction mixture. Reactor 5 is provided with indirect heat exchange means not shown. Coolant is introduced through conduit 6 into reactor 5 and passed in indirect heat exchange with the reactants and catalyst therein. The heat exchange coolant is withdrawn from reactor 5 through conduit 7. The reaction mixture is maintained at a temperature of about 90° F. and a pressure sufficient to provide liquid phase operations in reactor 5. Reaction mixture, comprising catalyst, alkylated hydrocarbons, unreacted hydrocarbons such as isobutane, and possibly some propylene, is withdrawn and passed via conduit 8 to a settler 9. In settler 9 high strength hydrogen fluoride catalyst is separated from a hydrocarbon phase containing alkylated hydrocarbons, unreacted hydrocarbons and possibly some alkyl fluoride compounds. The high strength hydrogen fluoride catalyst forms a separate heavier phase in a settler 9 and is withdrawn through conduit 10, passed through pump 13 and through conduit 14, and thus recycled to reactor 5. A small portion of the high strength catalyst in conduit 10 is withdrawn through conduit 11 and passed to a catalyst regeneration operation not shown. Fresh and/or regenerated catalyst containing a high concentration of hydrogen fluoride, e.g., 97 wt. percent is charged through conduit 12 to conduit 10 in order to maintain the catalyst employed in reactor 5 at an optimum strength. Referring again to settler 9, the hydrocarbon phase comprising alkylation reaction products, isobutane and possibly some alkyl fluoride, etc., is withdrawn and passed through conduit 15. The heavier olefinic reactant, comprising butylenes, is charged through conduit 16 into conduit 15 and admixed with the hydrocarbon materials in conduit 15. The admixed butylenes and hydrocarbon effluent from settler 9 are passed further through conduit 5 into reactor 19. Portions of the combined butylenes and hydrocarbon effluent in conduit 15 are diverted from conduit 15 to conduit 17 and conduit 18 and passed therethrough into reactor 19 in order to provide thorough mixing with alkylation catalyst in reactor 19. Reactor 19 is provided with indirect heat exchange means not shown. Coolant is charged to reactor 19 by way of conduit 20. The coolant is passed in indirect heat exchange with the reaction mixture in reactor 19 and subsequently withdrawn through conduit 21. The reactants charged to reactor 19 through conduits 15, 17 and 18 are admixed with low strength hydrogen fluoride catalyst, containing about 90 wt. percent acid, to form a reaction mixture in reactor 19. The reaction mixture in reactor 19 is maintained at a temperature of about 90° F. in liquid phase operations. After the alkylation reaction is substantially complete, reaction mixture is withdrawn from reactor 19 and passed through conduit 22 into reaction soaker 23, wherein the reaction mixture is maintained for an additional time at alkylation temperature and pressure. The mixture is withdrawn from the reaction soaker and passed through conduit 24 into settler 25. In settler 25, a heavier, low strength hydrogen fluoride catalyst phase separates and is withdrawn through conduit 26, passed through pump 29 and charged via conduit 30 to reactor 19. A small portion of the low strength catalyst in conduit 26 is withdrawn through conduit 27 and passed to regeneration not shown. Fresh and/or regenerated catalyst is charged through conduit 28 to conduit 26. Referring again to settler 25, a lighter, hydrocarbon phase, comprising alkylate product and unreacted isobutane, is withdrawn through conduit 31 and passed to conventional fractionation means, such as an isobutane stripper, for further conventional separation of the alkylate product, and preferably, recycle of the isobutane to reactor 5.

PREFERRED EMBODIMENTS OF THE INVENTION

The isoparaffinic and olefinic reactants which are preferably employed in the process of the present invention are well known in the art. Isobutane is the preferred isoparaffin although isopentane, isohexane, and the like, may be employed. A suitable isoparaffinic reactant may contain some non-reactive contaminants such as normal paraffins. For example, a typical commercial isobutane reactant may contain some propane and normal butane. The preferred heavier olefinic reactant comprises butylenes. A preefrred olefinic reactant may comprise, for example, pure butene-1, pure butene-2, pure isobutylene, or any mixture of two or all of the butylene isomers. Also preferred for use as the heavier olefinic reactant is a mixture of butylenes with some amylenes or other heavier olefinic reactants. Other suitable heavier olefinic reactants include $C_5$ and heavier olefins, but these may not provide results equivalent to those obtained with $C_4$ olefins. A preferred heavier olefinic feed stock may contain small amounts of such hydrocarbons as normal paraffins, isoparaffins, ethylene, propylene, etc.

The lighter olefinic reactant is preferably propylene, and may suitably be pure propylene or may contain small amounts of paraffins, isoparaffins, ethylene, butylenes, etc. A typical commercial propylene alkylation reactant contains propylene and propane. It is preferred that the heavier olefinic reactants be substantially free from the lighter olefin employed and, likewise, that the lighter olefinic reactant be substantially free from heavier olefin employed. By way of example, a typical preferred isoparaffinic feed stock may contain, for example 95 wt. percent isobutane, 1 wt. percent propane, and 4 wt. percent normal butane, while a typical preferred heavier olefinic reactant feed stock may contain about 40 wt. percent butylenes, 45 wt. percent isobutane and 15 wt. percent normal butane, and a typical preferred lighter olefinic reactant feed stock may contain 60 wt. percent propylene and 40 wt. percent propane.

Alkylation catalysts which can be utilized in the present invention, include alkylation catalysts known in the art. For example, strong acids such as hydrogen fluoride, sulfuric acid and phosphoric acid have all been employed. Other suitable catalysts include metal halides such as aluminum chloride, antimony halides, etc., boron halides, and certain crystalline aluminosilicates catalytically active for alkylation of isoparaffins, such as faujasite, mordenite, etc., either with or without the addition of catalytic amounts of metals or metal ions.

In general, hydrogen fluoride alkylation catalyst is preferred for use as an alkylation catalyst in the present process. Conventional hydrogen fluoride alkylation catalyst comprises about 75 wt. percent or more of titratable acid and about 5 wt. percent or less water, with the remainder made up of hydrocarbons and combined fluoride in solution in the acid. Such a conventional alkylation catalyst is suitable for use both as the alkylation catalyst in the first alkylation zone, for alkylating the isoparaffin with the lighter olefinic reactant, and in the second alkylation zone for use with the heavier olefinic reactant. In a particularly preferred embodiment of the process of this invention, two different strength hydrogen fluoride catalysts are employed. A higher strength alkylation catalyst is preferably utilized in the first alkylation zone to alkylate the isoparaffin with the lighter olefinic reactant, comprising preferably propylene. This higher strength catalyst is characterized by a concentration of titratable acid of about 80 wt. percent to about 99 wt. percent a water concentration of about 0.1 wt. percent to about 1 wt. percent and a hydrocarbon concentration of about 1 wt. percent to about 20 wt. percent. A different, lower strength hydrogen fluoride alkylation catalysts is preferably utilized in the second alkylation reaction zone in the reaction involving the heavier olefinic reactant, preferably comprising butylenes. The lower strength alkylation catalyst is characterized by a titratable acid concentration of about 65 wt. percent to about 95 wt. percent, a water concentration of about 0.1 wt. percent to about 1 wt. percent and a hydrocarbon concentration of about 5 wt. percent to about 35 wt. percent. A particularly preferred higher strength catalyst contains about 90 wt. percent to about 9 wt. percent acid while a particularly preferred lower strength catalyst contains about 80 wt. percent to about 95 wt. percent acid.

Numerous alkylation reaction zones suitable for use in the process of this invention are known in the art. For example, but not by way of limitation, the alkylation reactors described in U.S. Pats. 3,456,033, 3,469,949 and 3,501,536 may be suitably employed for both alkylation reactions when a fluid catalyst such as the preferred hydrogen fluoride catalyst is utilized. Isoparaffin-olefin alkylation conditions associated with the particular alkylation reactors described in the above-listed patents or in connection with other suitable conventional alkylation reactors, are also well known and may be used in particular embodiments of the present invention. The scope of the present invention is intended to include, for example, embodiments of the present process in which reactants and fluid catalysts are contacted in the alkylation zones and catalyst is subsequently separated from the reaction products by settling for further use. The scope of the present invention also includes embodiments wherein beds of a solid catalyst, such as a zeolitic catalyst, are employed in one or both of the reactors and the hydrocarbon effluent from the first reactor may thus be passed to the second reactor without further separation from the catalyst by settling. Particular alkylation zones and optimum alkylation conditions in specific embodiments of the present process depend upon the composition of the particular heavier olefinic reactant feed stream, the particular lighter olefinic reactant feed stream, the isoparaffin feed stream, and the type of catalyst employed. For example, in the preferred embodiment, isobutane and a lighter olefinic reactant comprising about 50 volume percent to about 70 volume percent propylene and about 30 volume percent to about 50 volume percent propane are contacted, at an isobutane/propylene mole ratio of about 5:1 to about 50:1, with a hydrogen fluoride catalyst in a first alkylation reaction zone at alkylation conditions including a temperature in the range from about 0° F. to about 200° F., a pressure sufficient to maintain the hydrocarbons and catalyst as liquids, a catalyst/hydrocarbon volume ratio in the first alkylation reactor in the range from about 0.1:1 to about 10:1 and a contact time (defined as the volume of the alkylation reactor divided by the volumetric flow rate, per minute of reactants and catalyst charged) in the first alkylation reactor in the range from about 0.1 minute to about 30 minutes. In this preferred embodiment, a heavier olefinic reactant comprising about 30 volume percent to about 60 volume percent butylenes with the remainder made up of propane and butanes, is contacted in a second alkylation reactor with the hydrocarbon effluent from the first alkylation zone, and with a hydrogen fluoride catalyst, at alkylation conditions including a temperature in the range from about 0° F. to about 200° F., a pressure sufficient to maintain liquid phase operations, a catalyst/hydrocarbon volume ratio, in the second alkylation reactor, of about 0.1:1 to about 10:1 and a contact time in the second alkylation reactor in the range from about 0.1 minute to about 30 minutes.

In a particularly preferred embodiment, alkylation conditions in the first alkylation zone include employment of the presferred high strength hydrogen fluoride alkylation catalyst described above and also include a temperature of about 60° F. to about 150° F., with a temperature of about 75° F. to about 120° F. particularly preferred, a pressure sufficient to maintain the reactants and catalyst as liquids, and a reaction time of about 0.1 minute to about 20 minutes. Preferably, in this particular embodiment, isobutane and propylene reactants are charged to the first alkylation reactor at a mole ratio of about 20:1 to about 30:1, and a catalyst-to-hydrocarbon volume ratio of about 0.5:1 to about 2:1 is maintained in the first alkylation zone. Likewise, in this particular preferred embodiment, alkylation conditions in the second alkylation reactor include the use of the preferred low strength hydrogen fluoride alkylation catalyst, as described above, and also include a temperature of about 40° F. to about 110° F., with a temperature of about 50° F. to about 100° F. particularly preferred, a pressure sufficient to maintain the reactants and catalyst as liquids, and a reaction time of about 0.1 minute to about 20 minutes. Preferably, the hydrocarbon effluent from the first alkylation zone and the heavier olefinic reactant, comprising butylenes, are charged to the second alkylation reactor at a butylenes-to-hydrocarbon effluent mole ratio of about 1:20 to about 1:30, and a catalyst-to-hydrocarbon volume ratio of about 0.5:1 to about 2:1 is maintained in the second alkylation reactor. By maintaining the above-described preferred conditions in the first alkylation zone and second alkylation zone respectively, when using propylene as the lighter olefinic reactant and butylenes as the heavier olefinic reactant, it is possible to provide an optimum yield of high quality alkylate product from both the propylene alkylation reaction and the butylenes alkylation reaction. The desirable high molar ratio of isobutane is also maintained in both the first and second alkylation reaction zones without the necessity of maintaining enough surplus isobutane to provide separate charges of excess isobutane to the separate reactors as taught in prior art. By employing the hydrocarbons, particularly isobutane, required in the second alkylation zone, the same charge of hydrocarbons acts, in part, as the excess required in both the lighter olefin alkylation reaction and the heavier olefin alkylation reaction. By utilizing propylene as the lighter olefinic reactant, and maintaining the above-described preferred alkylation conditions in the first alkylation zone, self-alkylation of isobutane, the preferred isoparaffin reactant, is enhanced. Under the preferred conditions employed in the first alkylation zone, propylene reacts with isobutane to provide propane and isobutylene, in what is known in the art as the hydrogen transfer reaction. The isobutylene thus formed reacts in an alkylation reaction with further isobutane to provide primarily high octane $C_8$ hydrocarbons. Thus, while more isobutane may be consumed in the preferred embodiment of the present process than in some conventional alkylation processes, the increased consumption would be more than offset by the products of additional amounts of superior alkylate product.

In the preferred embodiment, the reaction mixture formed in the second alkylation reactor is passed through a reaction soaker. In the description of the preferred embodiments herein provided, it is intended that both the second alkylation reactor and the reaction soaker, as well as a settler, are included within the scope of the term "second alkylation zone." Suitable reaction soakers are well known in the art. For example, the reaction soakers described in U.S. Pats. 3,560,587 and 3,607,970 may suitably be employed in the present process. Such reaction soakers are commonly vessels equipped with perforated trays, baffle sections, or the like, to maintain the mixture of catalyst and hydrocarbons charged from the second alkylation reactor as a fairly homogenous mixture at alkylation temperature and pressure for a predetermined length of time. The mixture of catalyst and hydrocarbons is maintained in the reaction soaker for a time which depends on the composition of the reaction mixture. A reaction soaker residence time of about 1 minute to about 30 minutes is preferred. The temperature and pressure maintained in the reaction soaker are the same as the temperature and pressure maintained in the second alkylation reactor.

Means for separating a hydrocarbon phase from, for example, a fluid catalyst phase, such as a hydrogen fluoride catalyst, in the effluent from an alkylation reactor or reaction soaker are well known in the alkylation art. Generally, when a fluid catalyst such as hydrogen fluoride is employed in the present process, the effluent from an alkylation reactor or soaker comprises a mixture of isoparaffin, reaction products, catalyst and catalyst-soluble organic materials with small amounts of olefin-acting compounds, light hydrocarbon gases, etc. When this mixture is allowed to stand unstirred, i.e., settled, the reaction products, isoparaffin, light hydrocarbon gases, and possibly some organic fluorides, from a hydrocarbon phase, possibly containing a small amount of catalyst in solution. The catalyst and catalyst-soluble hydrocarbons form a separate phase. The hydrocarbon phase is thus easily mechanically separated from the catalyst phase. The temperature and pressure maintained during such a settling operation in an alkylation process, required when a fluid catalyst is utilized, are substantially the same as those described in connection with alkylation reaction conditions employed in the reactor. The hydrocarbons and the catalyst are preferably maintained in the liquid phase during the separation operation. The term "alkylation zone" is intended to include a settler as well as a reactor, where a settler is required in order to separate the hydrocarbons from the catalyst, e.g., when hydrogen fluoride catalyst is employed.

Some means for withdrawing heat from the alkylation zones is usually necessary for satisfactory operation of the process. A variety of means for accomplishing the heat withdrawal are well known. For example, in a preferred embodiment the heat generated by the alkylation reaction may be withdrawn directly from the alkylation reactor by indirect heat exchange between cooling water and the reaction mixture in the reactor.

The hydrocarbon stream, or phase, recovered, in the preferred embodiment, from the first alkylation reactor by settling the reaction mixture effluent therefrom, is combined with the heavier olefinic reactant, preferably butylenes, and charged to the second alkylation reactor, wherein this combined hydrocarbons stream is contacted with an alkylation catalyst. It is contemplated that sufficient isoparaffin is charged to the first reactor so that no further isoparaffin need be added to the hydrocarbons charged to the second reactor. Generally, the total isobutane charged to the alkylation process is passed through, in turn, the first alkylation zone and the second alkylation zone. Under some conditions, it may be advantageous to charge some further isobutane to the second alkylation reactor, and such a modification is within the scope of this invention. The second hydrocarbons stream, recovered from the second alkylation zone, is passed to further conventional separation operations and equipment, such as a fractionator, whereby the alkylation product is separated from unconsumed isoparaffin and any entrained or dissolved catalyst such as hydrogen fluoride, if any, which is present in the hydrocarbons effluent from the second alkylation zone. Any suitable method utilized in the prior art to separate the alkylate product from the isoparaffin and, for example, hydrogen fluoride, may be employed in the present process.

The alkylation reaction product produced in the improved process of this invention includes primarily $C_7$ and $C_8$ saturated hydrocarbons resulting from the alkylation reactions of the isoparaffin with both the lighter and the heavier olefinic reactants. The primary products include, for example, dimethylpentanes and trimethylpentane. It is well known that more highly branched hydrocarbons possess superior properties as motor fuel, and the present invention is directed, in part, to providing alkylate from the process containing a higher ratio of more highly branched hydrocarbons, such as trimethylpentanes, to less branched hydrocarbons, such as dimethylhexanes. Thus, it is apparent that the present invention provides a novel process for producing a superior alkylate product by a method more economical and convenient than has been available in the prior art.

EXAMPLE I

A supply of mixed butylenes charge stock was obtained and analyzed. It was found to contain 50 wt. percent butene-2, 28 wt. percent isobutylene and 22 wt. percent butene-1. A supply of propylene charge stock was obtained and analyzed and found to contain 99.6 wt. percent propylene. A supply of isobutane charge stock was obtained, and analysis showed that it contained 96 wt. percent isobutane, 3 wt. percent normally butane and 1 wt. percent propane.

Organic catalyst diluent was prepared, as needed for use in alkylation catalysts by charging 4 liters of isobutylene and 1.6 liters of 99 wt. percent hydrogen fluoride to an 8.81 liter stirred autoclave under a 200 p.s.i. nitrogen atmosphere, allowing the olefin and catalyst to react for one hour at 60° C., and then separating the diluent from the acid. Analysis of the diluent showed that it comprised polyisobutylenes having a molecular weight in the range from about 200 to about 500.

In order to demonstrate the utility of the process of the present invention, a portion of the propylene charge stock was mixed with a portion of the isobutane charge stock at an isobutane/propylene mole ratio of 24:1. This mixture was continuously charged to an alkylation reactor at the rate of 0.5 mole propylene per hour and 12 moles isobutane per hour. Simultaneously, hydrogen fluoride alkylation catalyst containing 95 wt. percent hydrogen fluoride, 4 wt. percent organic diluent and 1 wt. percent water was also continuously charged to the reactor. The alkylation reactor was equipped with stirring means and means for removing excess heat of reaction. An acid/hydrocarbon volume ratio of 3/2 was maintained in the reactor. The reaction mixture formed in the alkylation reactor was maintained at a temperature of 105° F. and a pressure of 15 atmospheres. A residence time (defined as the volume of the reactor divided by the total volume of reactants and catalyst charged per minute) of 10 minutes was maintained. The reaction mixture was continuously withdrawn from the alkylation reactor, passed into a settling vessel, and held at a residence time of 5 minutes, whereby the mixture was separated into a catalyst phase and a hydrocarbon phase. The catalyst phase was recovered and recycled to the alkylation reactor for further use. The hydrocarbon phase was withdrawn from the settler and recovered. The hydrocarbons thus recovered from the settler were continuously charged to an alkylation reactor identical to the one used, as described above, to react the propylene. A portion of the above-described butylenes feed stock was admixed with the hydrocarbon phase and continuously charged to the alkylation reactor at the rate of 0.5 mole of $C_4$ olefins per hour. Simultaneously, hydrogen fluoride alkylation catalyst containing 75 wt. percent hydrogen fluoride, 24 wt. percent organic diluent and 1 wt. percent water was also charged to the alkylation reactor. An acid/hydrocarbon volume ratio of 3/2 was maintained in the reactor. The reaction mixture formed from the catalyst and hydrocarbons was held at a temperature of 90° F. and a pressure of 15 atmospheres for a residence time of 10 minutes. The reaction mixture was continuously withdrawn from the alkylation reactor, charged to a settling vessel and settled to provide a catalyst phase and a hydrocarbon phase. The catalyst phase was continuously removed and recycled to the alkylation reactor for further use. The hydrocarbon phase was continuously withdrawn from the settling vessel. The $C_5$ and heavier hydrocarbons in this hydrocarbon phase were separated and recovered as the product of the alkylation process. When this product was analyzed, it was found to have a clear research octane number of 95.2 and a clear motor octane number of 92.5.

EXAMPLE II

In order to demonstrate the superiority of the process of the present invention over other methods for alkylating isobutane with propylene and butylenes, a portion of the same butylenes charge stock used in Example I was mixed with a portion of the same isobutane charge stock used in Example I at an isobutane/$C_4$ olefins mole ratio of 24:1: This mixture was continuously charged to an alkylation reactor identical to those used in Example I at the rate of 0.5 mole of $C_4$ olefins per hour and 12 moles isobutane per hour. Simultaneously, hydrogen fluoride alkylation catalyst containing 5 wt. percent hydrogen fluoride, 24 wt. percent organic diluent and 1 wt. percent water was also continuously charged to the reactor. An acid/hydrocarbon volume ratio of 3/2 was maintained in the reactor. The reaction mixture formed in the alkylation reactor was maintained at a temperature of 90° F. and a pressure of 15 atmospheres for a residence time of 10 minutes. The reaction mixture was continuously withdrawn from the alkylation reactor, passed into a settling vessel and held therein for a residence time of 5 minutes, whereby a catalyst phase and a hydrocarbon phase were separated. The catalyst phase was withdrawn from the settler and recycled to the alkylation reactor for further use. The hydrocarbon phase was withdrawn from the settler and recovered. The hydrocarbons thus recovered from the settler were continuously charged to an alkylation reactor identical to the one used as described above. A portion of the same propylene charge stock used in Example I was admixed with the hydrocarbons from the settler and continuously charged with them to the reactor at a rate of 0.5 mole propylene per hour. Simultaneously, hydrogen fluoride alkylation catalyst containing 95 wt. percent hydrogen fluoride, 4 wt. percent organic diluent and 1 wt. percent water, was also continuously charged to the reactor. An acid/hydrocarbon volume ration of 3/2 was maintained in the reactor. The reaction mixture formed in the alkylation reactor was held at a temperature of 105° F. and a pressure of 15 atmospheres for a residence time of 10 minutes. The reaction mixture was continuously withdrawn from the alkylation reaction mixture was continuously withdrawn from the alkylation reactor, passed into a settling vessel and held for a residence time of 5 minutes, whereby the reaction mixture settled into a catalyst phase and a hydrocarbon phase. The catalyst phase was continuously withdrawn from the settling vessel and recycled to the reactor for further use. The hydrocarbon phase was continuously withdrawn from the settling vessel. The $C_5$ and heavier hydrocarbons in this hydrocarbon phase were separated and recovered as the product of the process. When this product was analyzed, it was found to have a clear research octane number of 94.5 and a clear motor octane number of 92.0.

By a comparison of the octane numbers of the alkylate product obtained as described in Example I with the octane numbers of the product obtained as described in Example II, it is evident that the method of the present invention, as embodied in Example I, is substantially and quite surprisingly superior to the method described in Example II. Although the reasons for the unexpected superiority of the alkylate product in Example I over that in Example II are not completely known, the superiority may be due, in part, to the degradation in the second reactor of the alkylate formed in the first reactor in Example II when it is subjected to the relatively severe conditions, ideal for alkylation of propylene, in the second reactor. Comparison of Example I with Example II further shows that merely by utilizing the first reactor to alkylate propylene and the second reactor to alkylate butylenes, rather than vice versa, even when identical reactors and reaction conditions are used, as in Example II, a substantially superior product may be recovered by the method of the present invention, while there is no increase in consumption of reactants, utilities, etc.

EXAMPLE III

In order to illustrate the flexibility of optimum alkylation conditions which may be employed for the alkylation of butylenes in the process of the present invention, a portion of the propylene charge stock described in Example I was combined with a portion of the isobutane charge stock also described in Example I at an isobutane/propylene mole ratio of 24:1. The combined isobutane and propylene were charged to an alkylation reactor identical to the reactor employed in Example I for the propylene-isobutane reaction. The isobutane and propylene were charged continuously to the reactor at an isobutane flow rate of 12 moles per hour and a propylene flow rate of 0.5 mole per hour. Hydrogen fluoride alkylation catalyst, containing 95 wt. percent hydrogen fluoride, 4 wt. percent organic diluent and 1 wt. percent water was also continuously charged to the reactor. The catalyst and hydrocarbons were contacted to form a reaction mixture and the reaction mixture was maintained at an acid/hydrocarbon volume ratio of 3/2, a temperature of 90° F. and a pressure of 15 atmospheres for a residence time of 10 minutes. Reaction mixture was continuously withdrawn from the reactor and passed to a settling vessel, wherein it was held for a residence time of 5 minutes, forming a catalyst phase and a hydrocarbon phase. The catalyst phase was continuously withdrawn from the settling vessel and recycled to the reactor for further use. The hydrocarbon phase was withdrawn from the settler and recovered. The hydrocarbons thereby recovered from the settler were continuously charged to an alkylation reactor identical to the one used, as described above, to react the propylene and isobutane. A portion of the butylenes feed stock described in Example I was admixed with the hydrocarbons and also continuously passed to the reactor. The butylenes were charged to the reactor at a flow rate of 0.5 mole per hour. Hydrogen fluoride alkylation catalyst, containing 89 wt. percent hydrogen fluoride, 9 wt. percent organic diluent and 1 wt. percent water, was simultaneously charged to the alkylation reactor. The hydrocarbons and catalyst were admixed to form a reaction mixture having an acid/hydrocarbon volume ratio of 3/2, and the reaction mixture was held at a temperature of 90° F. and a pressure of 15 atmospheres for a residence time of 10 minutes. Reaction mixture was continuously withdrawn from the reactor, passed to a settling vessel, and held therein for a residence time of 5 minutes, forming a catalyst phase and a hydrocarbon phase. The catalyst phase was continuously withdrawn from the settler and recycled to the reactor for further use. The hydrocarbon phase was withdrawan from the reactor. The $C_5$ and heavier hydrocarbons in the hydrocarbon phase were separated and recovered as the alkylate product. This alkylate product was analyzed and found to have a clear research octane of 96.2.

By contrasting the conditions employed and the quality of the alkylate produced in Example I with the conditions used and the quality of the alkylate of Example III, it can be seen that by varying the temperatures in the first reactor and second reactor, and by using a higher strength acid in the second reactor in Example III, a product of significantly higher quality was produced. This surprising result is particularly unexpected, since the quality of the alkylate produced in Example I is substantially higher than that of alkylate produced from the same reactants by conventional methods, and the quality of the alkylate of Example I was also substantially higher than alkylate produced by reversing the order of reaction of the propylene and butylenes, as described in Example II.

Examples I and III clearly demonstrate the wide range of conditions at which the present process, particularly the second, butylenes alkylation operation, may be performed. By adjusting the conditions in the second, butylenes stages of the process to provide optimum butylenes alkylation conditions, while maintaining the second stage conditions as mild as possible to prevent degradtion of the alkylate produced in the first, propylene alkylation stage, a particularly efficient and satisfactory process is achieved. This is particularly true in contrast to performing an alkylation process by the method of Example II, where propylene is reacted in the second stage. Propylene alkylation conditions, in general, are not as flexible as butylenes alkylation conditions. Further, the propylene alkylation conditions must, in general, be more severe than butylene alkylation conditions to provide a satisfactory product.

EXAMPLE IV

The superior flexibility of the process of the present invention in contrast to the method of Example II was further demonstrated by varying the alkylation conditions using the process of Example II. A portion of the same butylenes charge stock employed in Example I was mixed with a portion of the same isobutane charge stock as used in Example I. The mixture was made at a 24:1 isobutane/butylenes mole ratio. The isobutane-butylenes mixture was continuously charged to an alkylation reactor identical to those employed in Example I at a flow rate of 0.5 mole butylenes and 12 moles isobutane per hour. Hydrogen fluoride alkylation catalyst containing 75 wt. percent acid, 24 wt. percent organic diluent, and 1 wt. percent water was also continuously charged to the reactor. The catalyst and hydrocarbons were admixed at a catalyst/hydrocarbon volume ratio of 3/2. The reaction mixture was maintained at a temperature of 90° F. and a pressure of 15 atmospheres for a residence time of 10 minutes. Reaction mixture was continuously withdrawn and passed to a settling vessel and held therein for a 5-minute residence time. A catalyst phase and a hydrocarbon phase was thereby settled out. The catalyst phase was withdrawn from the settler and recycled to the reactor for further use in the butylenes alkylation reaction. The hydrocarbon phase was recovered from the settler and continuously passed to an alkylation reactor identical to the one used in the first stage. A portion of the same propylene charge stock used in Example I was admixed with the hydrocarbons recovered from the settler and was thereby also passed to the second stage reactor at a rate of 0.5 mole per hour. Hydrogen fluoride catalyst containing 95 wt. percent acid, 4 wt. percent organic diluent, and 1 wt percent water was simultaneously, continuously charged to the second stage reactor. A catalyst/hydrocarbon volume ratio of 3/2 was maintained. The mixture of hydrocarbons and catalyst was maintained at a temperature of 90° F. and a pressure of 15 atmospheres for a residence time of 10 minutes. Reaction mixture was continuously withdrawn from the second stage reactor, passed to a settler and held therein for a 5-minute residence time. A catalyst phase and a hydrocarbon phase were separated, and the catalyst phase was continuously withdrawn from the settler and recycled to the second stage reactor for further use. The hydrocarbon phase was withdrawn from the settler and fractionated. The $C_5$ and heavier hydrocarbons were separated from the lighter hydrocarbons and recovered as the alkylate product of the process. When the alkylate product was analyzed, it was found to have a clear research octane number of 95.

Contrasting Examples I and III, wherein propylene is alkylated in the first stage and butylenes are alkylated in the second stage, according to the process of the present invention, with Examples II and IV, wherein butylenes are alkylated in the first stage and propylene in the second, it is apparent that the process of the present invention has greater flexibilty and provides a clearly superior alkylate product. In both Examples III and IV, propylene was alkylated utilizing the same temperature and acid strength, and the second stage in both these examples was operated at a temperature of 90° F. Yet the method of Example III, employing the present inventive process, produced a clearly superior alkylate product. By adjusting reaction conditions, Example IV produced only a one-half research octane number increase in the alkylate product over Example II. In contrast, by adjustment of the alkylation reaction conditions in Example III, an octane number increase of one number was achieved over the alkylate of Example I. Further, even by adjusting reaction conditions in Example IV, the method of the present invention used in Example I to provide an alkylate product having an octane number at the lower end of the range obtained using the present process, provided an alkylate product superior to that obtained by the method of Examples II and IV.

EXAMPLE V

In order to illustrate some of the advantages of the process of the present invention over conventional methods for producing alkylate, a conventional operation is performed. Portions of the propylene charge stock and isobutane charge stock described in Example I are combined at an isobutane/propylene mole ratio of 12 to 1. The reactants are contuously charged to an alkylation reactor identical to the one used to alkylate propylene in Example I. The flow rate of reactants is maintained at 6 moles per hour of isobutane and 0.5 mole per hour of propylene. Hydrogen fluoride alkylation catalyst, containing 95 wt. percent hydrogen fluoride, 4 wt. percent organic diluent and 1 wt. percent water, is also continuously charged to the reactor. The hydrocarbons and catalyst are admixed at an acid/hydrocarbon volume ratio of 3/2 and the reaction mixture is maintained at a temperature of 90° F. and a pressure of 15 atmospheres for a residence time of 10 minutes. The reaction mixture is continuously withdrawn from the reactor and passed to a settling vessel. The reaction mixture is held in the settler for a residence time of 5 minutes, whereby a catalyst phase and a hydrocarbon phase are formed. The catalyst phase is withdrawn from the settler and recycled to the reactor for further use. The hydrocarbon phase is withdrawn from the settler and recovered. Portions of the butylenes charge stock and isobutane charge stock described in Example I are combined at an isobutane/butylenes mole ratio of 12 to 1. These reactants are continuously charged to an alkylation reactor, identical to the one used to alkylate butylenes in Example I, at an isobutane flow rate of 6 moles per hour and a butylenes flow rate of 0.5 mole per hour. Hydrogen fluoride alkylation catalyst, containing 90 wt. percent hydrogen fluoride, 9 wt. percent organic diluent and 1 wt. percent water is also charged continuously to the reactor and combined with the hydrocarbon charge at an acid/hydrocarbon volume ratio of 3/2. The resulting reaction mixture is held at a temperature of 90° F. and a pressure of 15 atmospheres for a residence time of 10 minutes. Reaction mixture is continuously withdrawn from the reactor, passed to a settler, and separated therein into a catalyst phase and a hydrocarbon phase. A residence time in the settler of 5 minutes is maintained. The catalyst phase is continuously withdrawn from the settler and recycled to the reactor for further use. The hydrocarbon phase is withdrawn from the settler and combined with the hydrocarbon phase recovered from the propylene alkylation settler described above. The $C_5$ and heavier hydrocarbons from this combined hydrocarbon phase are separtaed from the lighter hydrocarbons and recovered as the product of the process. This alkylate product is analyzed and found to have a clear research octane number of 94.5.

By comparing the quality of the alkylate produced in Example V with the quality of the alkylates produced in Example I and Example III, it can be seen that the process of the present invention is capable of producing a substantially superior alkylate product. Comparing the amount of reactants charged in Examples I and III with the amount of reactants charged in Example V shows that the exact same amounts of reactants were used in all three examples, with substantially the same alkylation conditions used in the reactors. Thus, the superiority of the process of this invention is clearly demonstrated.

EXAMPLE VI

The process of the present invention is further compared with conventional alkylation techniques by performing a typical conventional alkylation process wherein the propylene and butylene reactants are combined. The same propylene, butylene, and isobutane reactants as employed in Example I are utilized. The reactants are admixed to provide a 24:1 isobutane/propylene mole ratio, a 24:1 isobutane/butylenes mole ratio and an overall isobutane/olefins mole ratio of 12:1. The reactants are continuously charged to an alkylation reactor identical to those employed in Example I. A flow rate of 12 moles per hour of isobutane, 0.5 mole per hour of butylenes and 0.5 mole per hour of propylene is maintained. Simultaneously, hydrogen fluoride catalyst containing 89 wt. percent acid, 10 wt. percent organic diluent and 1 wt. percent water is also charged to the reactor. A 3/2 volume ratio of catalyst to hydrocarbons is maintained in the reaction mixture. A temperature of 90° F. and a pressure of 15 atmospheres are also maintained. After a residence time of 10 minutes, the reaction mixture is continuously withdrawn from the reactor, passed to a settler, and held therein for 5 minutes residence time. The resulting catalyst phase is withdrawn from the settler and recycled to the reactor for further use. The hydrocarbon phase resulting from the settling operation is withdrawn from the settler and fractionated. The $C_5$ and heavier hydrocarbons in the hydrocarbon phase are separated and recovered as the alkylate product of the process. This alkylate product is analyzed and found to have a clear research octane number of 93.5.

Comparing the alkylate product produced, according to the process of the present invention, by the methods in Examples I and III, with the alkylate product produced by the conventional alkylation technique of Example VI, it is apparent that the present process provides a surprising and substantial improvement in the quality of the alkylate recovered, while using the same amounts of reactants. Using identical amounts of the olefinic reactants and isobutane, the method of Example III produced an alkylate having a research octane number of 96.2, while the conventional, commercial method of Example VI produced an alkylate having a research octane number of only 93.5.

EXAMPLE VII

A process according to the present invention, identical to that used in Example III, was employed, the only difference being that a temperature of 68° F. was maintained in the second stage reactor wherein the butylenes reactant was alkylated, in contrast to Example III, in which a temperature of 90° F. was employed. The hydrocarbons removed from the second stage settler were separated into a $C_5$+fraction and a $C_4$ and lighter fraction. The $C_5$+ fraction was recovered as the alkylate product of the operation and analyzed. It was found to have a research octane number of 96.2, identical to that of the alkylate produced by the method of Example III. Thus, the flexibility of the conditions which may be employed to alkylate butylenes according to the process of the present invention was further demonstrated.

EXAMPLE VIII

In a further demonstration of the utility of the process of the present invention, the alkylate products produced in Examples II, III, and VII were further analyzed to determine the friction of $C_9$ and heavier hydrocarbons produced by the embodiments of these examples. It was found that the alkylate product produced in Examples III and VII, by the process of the present invention, contained only 4 wt. percent $C_9$ and heavier hydrocarbons, while the product produced using the method of Example II, by merely reversing the order of reaction of the lighter and heavier olefins from the order taught according to the process of this invention, contained 6.2 wt. percent $C_9$ and heavier hydrocarbons. The alkylate product obtained by the conventional processes of Examples V and VI is also analyzed and found to comprise 5 wt. percent $C_9$ and heavier hydrocarbons. It is thus apparent that the process of the invention provides a method for producing an alkylate product having an end boiling point substantially below the end points of alkylates obtained using prior art and other alkylation processes.

I claim as my invention:

1. A process for producing an alkylation reaction product from an isoparaffin reactant, a lighter olefinic reactant and a heavier olefinic reactant which comprises the steps of:

(a) contacting said isoparaffinic reactant and said lighter olefinic reactant with a first *hydrogen fluoride* alkylation catalyst in a first alkylation zone at first alkylation conditions;

(b) settling from said first alkylation zone a first hydrocarbon phase which comprises a portion of said isoparaffinic reactant and a portion of said alkylation reaction product;

(c) contacting said heavier olefinic reactant and at least a portion of said first hydrocarbon phase with a second *hydrogen fluoride* alkylation catalyst in a second alkylation zone at second alkylation conditions;

(d) settling from said second alkylation zone a second hydrocarbon phase which comprises at least a portion of said alkylation reaction product; and, (e) recovering said alkylation reaction product from said second hydrocarbon phase.

2. The process of claim 1 wherein said lighter olefinic reactant comprises propylene.

3. The process of claim 1 wherein said heavier olefinic reactant comprises butylenes.

[4. The process of claim 1 wherein said first alkylation catalyst is hydrogen fluoride alkylation catalyst.]

[5. The process of claim 1 wherein said second alkylation catalyst is hydrogen fluoride alkylation catalyst.]

6. The process of claim [4] *1* wherein said first *hydrogen fluoride* alkylation catalyst [is a hydrogen fluoride alkylation catalyst comprising] *comprises* about 80 wt. percent to about 99 wt. percent hydrogen fluoride and said first alkylation conditions include a temperature of about 60° F. to about 150° F.

7. The process of claim [5] *1* wherein said second *hydrogen fluoride* alkylation catalyst [is a hydrogen fluoride alkylation catalyst comprising] *comprises* about 65 wt. percent to about 95 wt. percent hydrogen fluoride and said second alkylation conditions include a temperature of about 0° F. to about 110° F.

8. The process of claim 1 wherein an isoparaffinc recycle stream is recovered from said second hydrocarbon phase and at least a portion of said isoparaffinic recycle stream is introduced into said first alkylation zone.

9. The process of claim 1 wherein said isoparaffinic reactant comprises isobutane.

[10. The process of claim 1 wherein said first alkylation catalyst is selected from sulfuric acid, phosphoric acid and a crystalline aluminosilicate catalytically active for isoparaffin-olefin alkylation.]

[11. The process of claim 1 wherein said second alkylation catalyst is selected from sulfuric acid, phosphoric acid and a crystalline aluminosilicate catalytically active for isoparaffin-olefin alkylation.]

12. The process of claim 6 wherein said first alkylation conditions include a temperature of about 75° F. to about 120° F. and said first *hydrogen fluoride* alkylation catalyst comprises about 85 wt. percent to about 99 wt. percent hydrogen fluoride.

13. The process of claim 7 wherein said second alkylation conditions include a temperature of about 50° F. to about 100° F. and said second *hydrogen fluoride* alkylation catalyst comprises about 70 wt. percent to about 95 wt. percent hydrogen fluoride.

* * * * *